United States Patent
Reigl

(10) Patent No.: US 10,151,216 B2
(45) Date of Patent: Dec. 11, 2018

(54) INSULATION QUALITY INDICATOR MODULE FOR A VALVE AND ACTUATOR MONITORING SYSTEM

(71) Applicant: General Electric Technology GmbH, Baden (CH)

(72) Inventor: Martin Reigl, Ehrendingen (CH)

(73) Assignee: General Electric Technology GmbH, Baden (CH)

( * ) Notice: Subject to any disclaimer, the term of this patent is extended or adjusted under 35 U.S.C. 154(b) by 338 days.

(21) Appl. No.: 15/252,527

(22) Filed: Aug. 31, 2016

(65) Prior Publication Data

US 2018/0058252 A1 Mar. 1, 2018

(51) Int. Cl.
| | |
|---|---|
| *G01M 19/00* | (2006.01) |
| *F01D 21/00* | (2006.01) |
| *F01D 17/14* | (2006.01) |
| *F01D 17/20* | (2006.01) |
| *F01D 25/14* | (2006.01) |

(Continued)

(52) U.S. Cl.
CPC ......... *F01D 21/003* (2013.01); *F01D 17/145* (2013.01); *F01D 17/20* (2013.01); *F01D 21/12* (2013.01); *F01D 25/145* (2013.01); *F01D 25/24* (2013.01); *G01J 5/0088* (2013.01); *G01N 25/72* (2013.01); *F05D 2220/31* (2013.01); *F05D 2230/80* (2013.01); *F05D 2260/80* (2013.01); *F05D 2270/3032* (2013.01); *G01J 2005/0081* (2013.01)

(58) Field of Classification Search
USPC .......................................... 73/112.01, 112.02
See application file for complete search history.

(56) References Cited

U.S. PATENT DOCUMENTS 5,336,542 A * 8/1994 Wirth .................... F01D 25/145
428/116
6,655,409 B1 12/2003 Steenburgh et al.
(Continued)

FOREIGN PATENT DOCUMENTS

| JP | S57-200604 A | 12/1982 |
|---|---|---|
| JP | 2013-189864 A | 9/2013 |

OTHER PUBLICATIONS

Emerson Process Management, "ValveLink(TM) Software Signature Series Performance Testing", ValveLink Software D102687X102, Product Bulletin 62.1:ValveLink Software(S2), Oct. 2012, pp. 1-2, Fisher Controls International LLC, US.

(Continued)

*Primary Examiner* — Eric S McCall
(74) *Attorney, Agent, or Firm* — Eversheds Sutherland (US) LLP

(57) ABSTRACT

The present application provides a method of evaluating insulation quality in a turbine by a data acquisition system. The method may include the steps of receiving a number of operating parameters from a number of sensors, wherein the operating parameters may include casing temperatures and insulation temperatures, comparing the casing temperatures and the insulation temperatures to predetermined casing and insulation values, and altering one or more of the operating parameters and/or initiating repair procedures if the casing temperatures fall below the casing predetermined values and/or the insulation temperatures exceed the insulation predetermined values.

15 Claims, 16 Drawing Sheets

(51) Int. Cl.
*F01D 25/24* (2006.01)
*G01J 5/00* (2006.01)
*G01N 25/72* (2006.01)
*F01D 21/12* (2006.01)

(56) References Cited

U.S. PATENT DOCUMENTS

| | | | |
|---|---|---|---|
| 7,090,393 B2* | 8/2006 | Loy | F01D 11/00 374/144 |
| 7,223,065 B2 | 5/2007 | Suter | |
| 7,596,428 B2 | 9/2009 | Potdar et al. | |
| 7,650,908 B2 | 1/2010 | Seaton | |
| 8,005,575 B2 | 8/2011 | Kirchhof | |
| 8,064,158 B1 | 11/2011 | Carter et al. | |
| 8,522,820 B2 | 9/2013 | Biwanski et al. | |
| 8,622,083 B2 | 1/2014 | Reigl et al. | |
| 9,087,074 B2 | 7/2015 | Dalal | |
| 9,255,649 B2 | 2/2016 | Coleman et al. | |
| 9,279,345 B2 | 3/2016 | Chowdhury | |
| 2008/0243287 A1 | 10/2008 | Potdar et al. | |
| 2010/0227198 A1* | 9/2010 | Lampenscherf | C23C 30/00 428/702 |
| 2011/0285367 A1 | 11/2011 | Carter et al. | |
| 2012/0151922 A1 | 6/2012 | Koller et al. | |
| 2012/0323530 A1 | 12/2012 | Mazzaro et al. | |
| 2013/0104516 A1 | 5/2013 | Varillas et al. | |
| 2013/0305719 A1 | 11/2013 | Reigl | |
| 2014/0294561 A1 | 10/2014 | Toulemonde et al. | |
| 2015/0240968 A1 | 8/2015 | Coleman et al. | |
| 2015/0286205 A1 | 10/2015 | Menet | |
| 2015/0325060 A1 | 11/2015 | Tart et al. | |
| 2016/0033321 A1 | 2/2016 | Picand et al. | |
| 2017/0009658 A1* | 1/2017 | Kippel | F02C 3/04 |
| 2018/0058249 A1* | 3/2018 | Reigl | F01D 17/145 |
| 2018/0058253 A1* | 3/2018 | Reigl | F01D 21/003 |

OTHER PUBLICATIONS

Emerson Process Management, "Dead Band Plus Hysteresis Estimation with ValveLink(TM) Diagnostics", ValveLink Software D103549X012, Product Bulletin 62.1:ValveLink Software(S3), Oct. 2012, pp. 1-4, Fisher Controls International LLC, US.

Fisher-Rosemount, "Fieldvue Instrumentation VL2000 Series ValveLink(R) Software", ValveLink Software, Bulletin 62.1:VL2000, Sep. 1999, pp. 1-12, Fisher Controls, US.

Emerson Process Management, "ValveLink(TM) Software", ValveLink Software D102227X012, Product Bulletin 62.1:ValveLink Software, Nov. 2010, pp. 1-13, Fisher Controls International LLC, US.

International Search Report and Written Opinion issued in connection with corresponding PCT Application No. PCT/EP2017/071762 dated Dec. 21, 2017.

* cited by examiner

US 10,151,216 B2

INSULATION QUALITY INDICATOR MODULE FOR A VALVE AND ACTUATOR MONITORING SYSTEM

TECHNICAL FIELD

The present application and resultant patent relate generally to monitoring and control systems for steam turbines and other types of turbomachinery and more particularly relate to a valve and actuator monitoring system for steam turbines and the like that provides continuous component and system status information, warnings, and corrections.

BACKGROUND OF THE INVENTION

A steam turbine converts the kinetic or thermal energy of pressurized steam into useful mechanical work. Generally described, the steam is created in a steam generator or a boiler, passes through control valves and stop valves into the sections, and drives a rotor assembly. The rotor assembly then in turn may drive a generator to produce electrical energy and the like. The control valves and the stop valves control the operation of the steam turbine by controlling the flow of the steam into the sections. A control valve typically controls or regulates the volumetric flow and/or the pressure of the steam entering into the sections during normal operation levels. A stop valve is typically a safety valve. The stop valve is typically held open during normal operation and closed when immediate shutdown is necessary. In some applications, the control valve and the stop valve may be integrated into a single unit.

Due to market demands, steam turbines may be required to operate with increased cycling and longer inspection intervals. In order to obtain significant information about the condition of the steam turbine components, such as the control valves and the stop valves, condition monitoring systems may be used. Such monitoring systems, however, may be limited in scope in that certain types of component wear or damage may only be apparent via visual inspection during a system shutdown. Such outage costs and time may be significant.

SUMMARY OF THE INVENTION

The present application and the resultant patent provide a method of evaluating insulation quality in a turbine by a data acquisition system. The method may include the steps of receiving a number of operating parameters from a number of sensors, wherein the operating parameters may include casing temperatures and insulation temperatures, comparing the casing temperatures and the insulation temperatures to predetermined casing and insulation values, and altering one or more of the operating parameters and/or initiating repair procedures if the casing temperatures fall below the casing predetermined values and/or the insulation temperatures exceed the insulation predetermined values.

The present application and the resultant patent further provide a turbine system. The turbine system may include a number of valves, a number of sensors capable of receiving turbine and valve operating parameters, and a data acquisition system, including a processor in communication with the sensors. The data acquisition system is operable to perform the following operations: receiving the turbine and valve operating parameters from the sensors, wherein the turbine and valve operating parameters may include casing temperatures and insulation temperatures, comparing the casing temperatures and the insulation temperatures to predetermined values, and providing a warning if the casing temperatures and/or the insulation temperatures exceed or fall below the predetermined values.

These and other features and improvements of the present application and resultant patent will become apparent to one of ordinary skill in the art upon review of the following detailed description when taken in conjunction with the several drawings and the appended claims.

DETAILED DESCRIPTION

Figure 1:
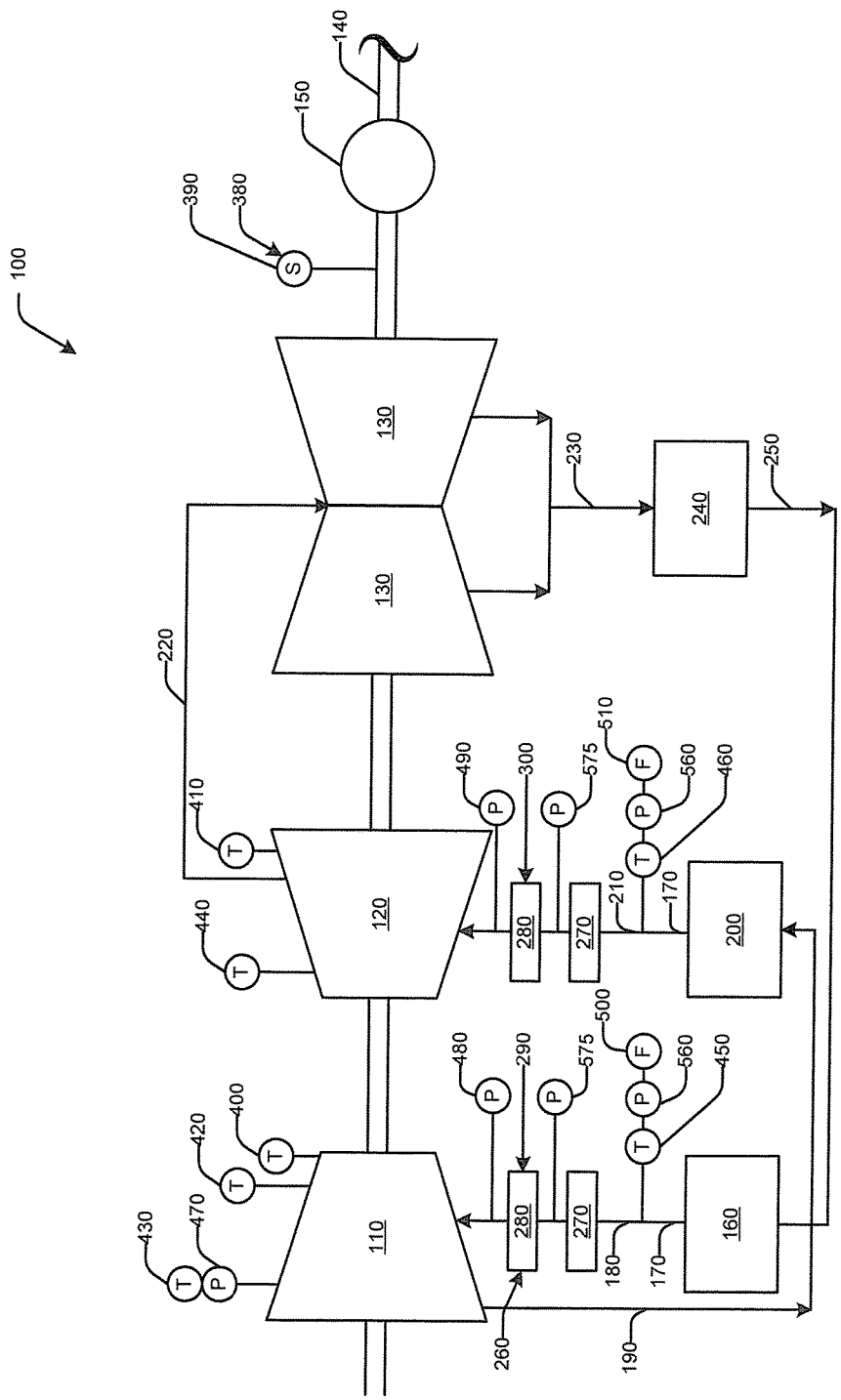
FIG. 1 is a schematic diagram of a steam turbine system as may be described herein.

Referring now to the drawings, in which like numerals refer to like elements throughout the several views, FIG. 1 is a schematic diagram of a steam turbine system 100 as may be described herein. Generally described, the steam turbine system 100 may include a high pressure section 110, an intermediate pressure section 120, and a low pressure section 130. The high pressure section 110, the intermediate pressure section 120, and the low pressure section 130 may be positioned on and may drive a rotor shaft 140. The rotor shaft 140 also may drive a generator 150 for the production of electrical power or for other types of useful work. The steam turbine system 100 may have any suitable size, shape, configuration, or capacity.

A boiler 160 and the like may produce a flow of steam 170. The boiler 160 and the flow of steam 170 may be in communication with the high pressure section 110 via a high pressure line 180. The steam 170 may drive the high pressure section 110 and exit the high pressure section 110 via a cold reheat line 190. The cold reheat line 190 may be in communication with a reheater 200 (i.e., the boiler 160 or part thereof). The reheater 200 may reheat the flow of steam 170. The reheater 200 and the flow of steam 170 may be in communication with the intermediate pressure section 120 via an intermediate pressure line 210. The flow of steam 170 may drive the intermediate pressure section 120 and may exit the intermediate pressure section 120 via a low pressure line 220. The flow of steam 170 then may drive the low pressure section 130 and may exit via a condenser line 230 to a condenser 240. The now condensed flow of steam 170 then may be returned to the boiler 160 or directed elsewhere. Other types of cycles and other types of components may be used herein.

Figure 2:
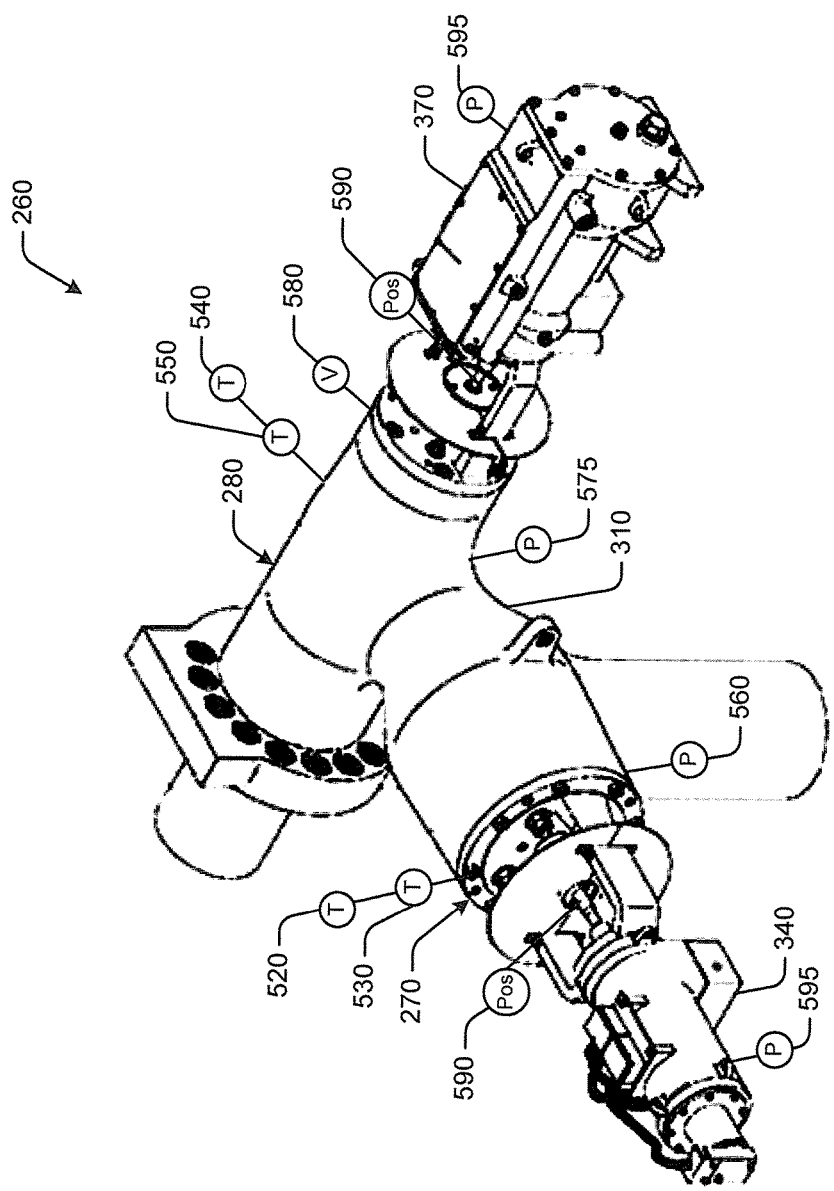
FIG. 2 is a partial perspective view of a combined stop valve and control valve that may be used with the steam turbine system of FIG. 1.
Figure 3:
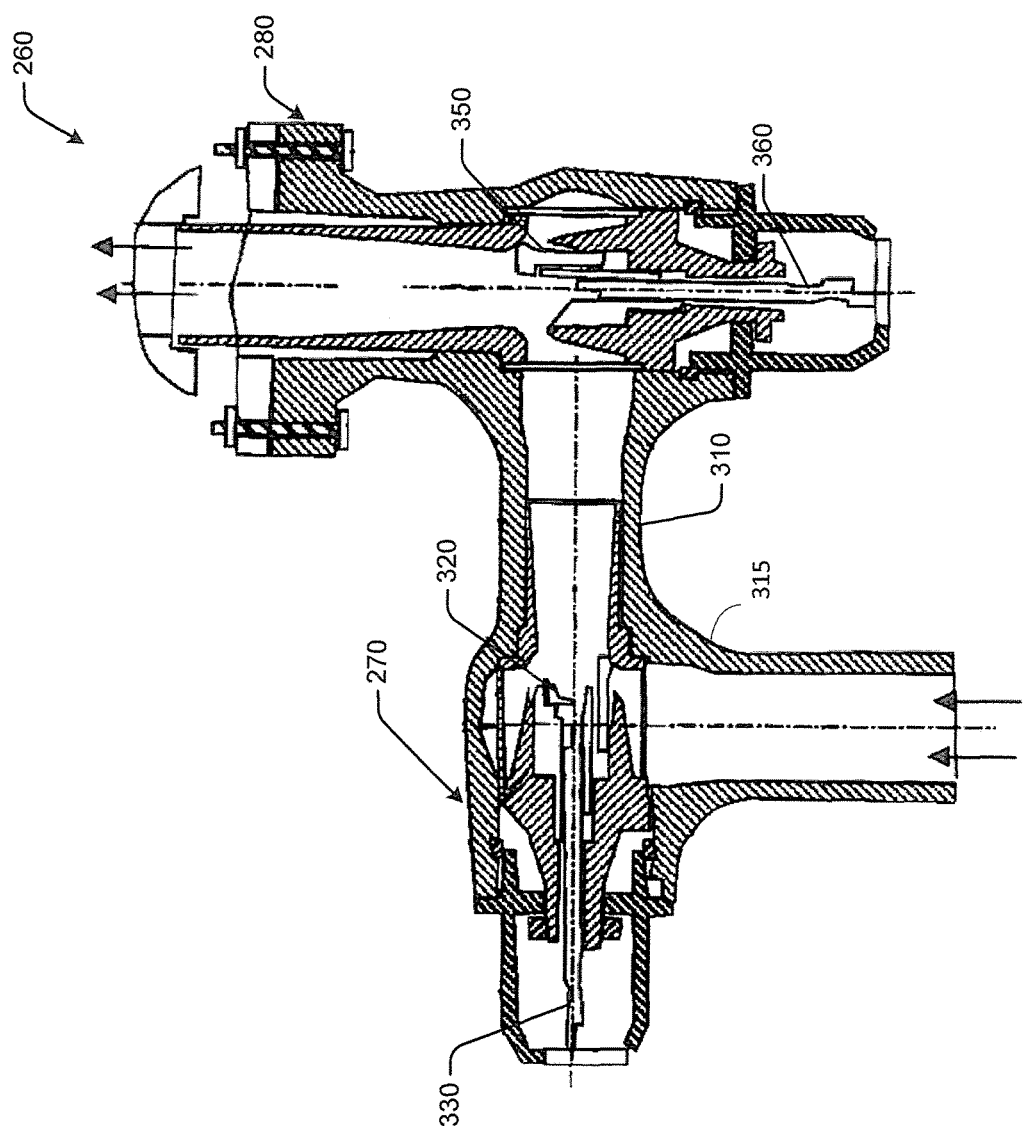
FIG. 3 is a partial cross-sectional view of the combined stop valve and control valve of FIG. 2.

The steam turbine system 100 may include a number of steam valves 260. The steam valves 260 may include a stop valve 270 and a control valve 280. Specifically, a high pressure stop valve and control valve 290 may be positioned on the high pressure line 180 while an intermediate pressure stop and control valve 300 may be positioned on the intermediate pressure line 210. Other types of valves and other locations may be used herein. As is shown in FIG. 2 and FIG. 3, the stop and control valves 290, 300 may include the stop valve 270 and the control valve 280 positioned within a common casing 310. The casing 310 may include one or more layers of insulation 315. The stop valve 270 may include a stop valve closing member 320. The stop valve closing member 320 may be driven by a stop valve spindle 330. The stop valve spindle 330 may in turn be driven by a stop valve actuator 340. Similarly, the control valve 280 may include a control valve closing member 350, a control valve spindle 360, and a control valve actuator 370. The steam valves 260 described herein are for the purpose of example only. Many other types of steam valves 270 and components thereof may be used herein in any suitable size, shape, or configuration.

The steam turbine system 100 may include a number of sensors 380. The sensors 380 may be of conventional design and may gather data on any type of operational parameter and the like. By way of the example only, the sensors 380 may include a speed sensor 390. The speed sensor 390 may be positioned about the rotor shaft 140 so as to determine the speed and acceleration thereof. The sensors 380 may include a number of metal temperature sensors such as a high pressure section metal temperature sensor 400 and an intermediate pressure section metal temperature sensor 410. The metal temperature sensors 400, 410 may be positioned about the rotor shaft 140 in the high pressure section 110 and the intermediate pressure section 120. The sensors 380 also may include a number of steam temperature sensors. The steam temperature sensors may include a high pressure section inlet temperature sensor 420 and a high pressure section outlet temperature sensor 430 positioned about the high pressure section 110 and an intermediate pressure section inlet temperature sensor 440 positioned about the intermediate pressure section 120. The steam temperature sensors also may include a high pressure valve temperature sensor 450 positioned about the high pressure stop and control valve 290 and an intermediate pressure valve temperature sensor 460 positioned about the intermediate pressure stop and control valve 300. The sensors 380 may include a number of steam pressure sensors. The steam pressure sensors may include a high pressure section exhaust pressure sensor 470 positioned about the high pressure section 110, a high pressure valve pressure sensor 480 positioned downstream of the high pressure stop and control valve 290, and an intermediate pressure valve pressure sensor 490 positioned downstream of the intermediate pressure stop and control valve 300. The sensors 380 also may include a number of mass flow sensors. The mass flow rate sensors may include a high pressure valve flow rate sensor 500 positioned about the high pressure stop and control valve 290 and an intermediate pressure valve flow rate sensor 510 positioned about the intermediate pressure stop and control valve 300.

The stop and control valves 290, 300 themselves also may include a number of sensors. These valves may include a stop valve inner casing temperature sensor 520 at an inner wall, a stop valve outer casing temperature sensor 530 at an outer wall, a control valve inner casing temperature sensor 540 at an inner wall, and a control valve outer casing temperature sensor 550 at an outer wall. The stop valve 270 may have an inlet pressure sensor 5600. A middle pressure sensor 575 may be positioned between the stop valve 270 and the control valve 280. The control valve spindle 360 may include a vibration sensor 580 while the actuators 340, 370 may have a position sensor 590 positioned on the shafts therein as well as a hydraulic pressure valve 595. The sensors 380 described herein are for the purpose of example only. Many other and different types of sensors also may be used herein.

Figure 4:
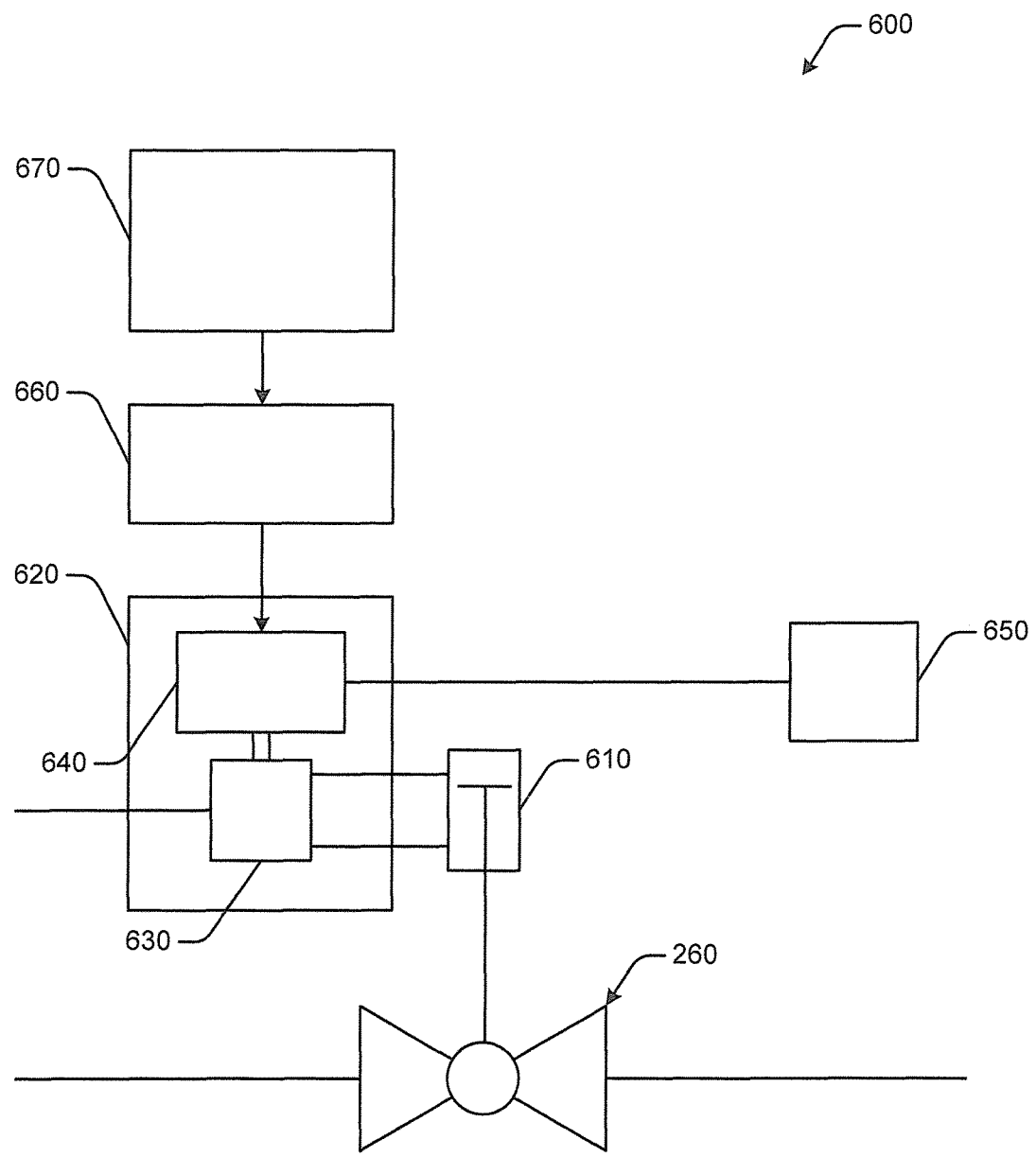
FIG. 4 is a schematic diagram of a distributed control system for use with the combined stop valve and control valve of FIG. 2.

FIG. 4 shows an example of an existing valve control system 600. The valve control system 600 may be used with any of the steam valves 260 described above and the like. As shown above, the steam valve 260 may be operated via an actuator 610. The actuator 610 may be of conventional design. Specifically, the steam valve 260 may be controlled via an electro-hydraulic converter 620. The electro-hydraulic converter 620 may include a converter valve 630 and a valve controller 640. The electro-hydraulic converter 620 converts an electric control signal into a corresponding hydraulic pressure for the actuator 610. The electro-hydraulic converter 620 may be of conventional design. The valve controller 640 may be in communication with installation and commissioning tool 650. The installation and commissioning tool 650 may be a conventional microprocessor and the like. The installation commissioning tool 650 may be used for valve set up and for periodic measurements. The installation and commissioning tool 650 may be connected to the electro-hydraulic converter 620 on request. Any number of the steam valves 260 may be controlled via a turbine governor 660 in communication with a distributed control system 670. The current valve control system 600 does not provide online monitoring or integration into existing monitoring systems. Input from the various sensors 380 may be in communication with the turbine governor 660 and/or the distributed control system 670 as may be required. Other components and other configurations may be used herein.

Figure 5:
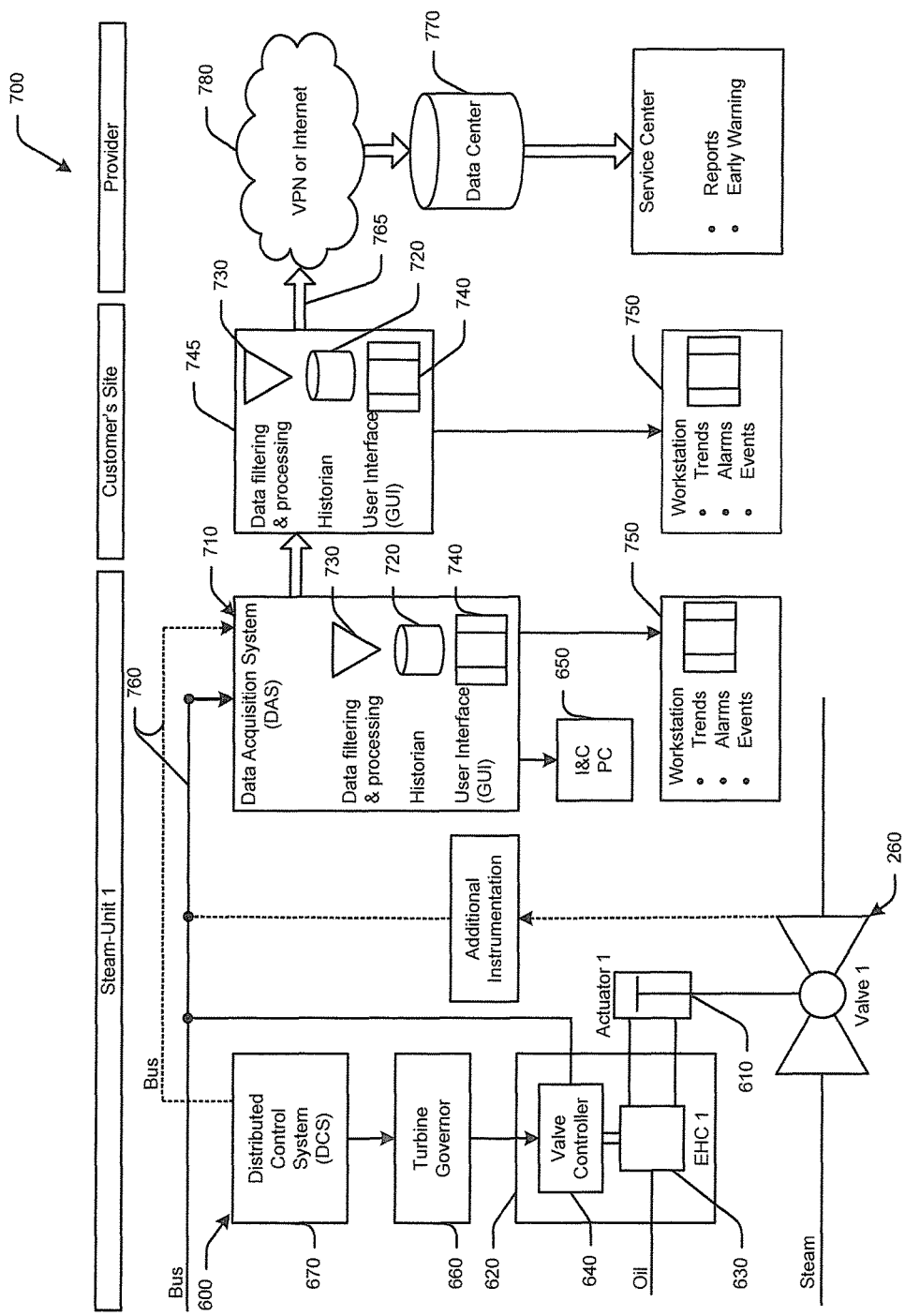
FIG. 5 is a schematic diagram of a Valve and Actuator Monitoring System ("VAMS") as may be described herein.

FIG. 5 shows an example of a valve and actuator monitoring system 700 as may be described herein (hereinafter "VAMS 700"). VAMS 700 assess the condition of the steam valves 260 based on continuous monitoring. VAMS 700 may provide real time monitoring of the steam valves 260 for condition assessment, predictive maintenance, correction, ordering spare parts, and the like. VAMS 700 may include a data acquisition system 710. Elements of the data acquisition system 710 may be used to acquire operational data of the steam valves 260 and control operation thereof and operational data of the steam turbine and the steam plant.

The data acquisition system 710 may include a historian 720. The historian 720 may be software and may or may not include database functions. The historian 720 interfaces with programmed logic via calculators and runs on data available therein. The historian 720 may store data received from the sensors 380 and the like and processed data. The historian 720 may be able to record non-scalar data as well as scalar data. (The valve controller 640 and the like may provide high speed recording for events with data output in a non-scalar format.) Other types of databases and platforms may be used herein. The data acquisition system 710 may import programmed logic implemented by software, hardware, firmware, or any combination thereof. The historians 720 may be cascaded such that one historian 720 may run on a server and collect data from a number of VAMS 700. Likewise, multiple data acquisition systems 710 may be used such that different features described herein may be executed on one or more of such different systems.

The data acquisition system 710 also may include a processor 730. The processor 730 may provide data filtering and processing. The processor 730 may utilize an operating system to execute program logic and, in doing so, also may utilize the measured data found on the historian 720. The processor 730 may include a calculator for computations. The calculator may be a freely programmable computation engine and can be written for the historian 720. The program languages may include Python, C/C++, and the like. The data acquisition system 710 receives available data and makes computation as to the assessment thereof.

Users may interface with the data acquisition system 710 via a graphical user interface 740. The graphical user interface 740 may include a display, keyboard, keypad, a mouse, control panel, a touch screen display, a microphone, and the like so as to facilitate user interaction. Specifically, the graphical user interface 740 may support a work station 750 wherein the data acquisition system 710 may provide trends, alarms, events, and the like. Data output by the data acquisition system 710 may be available to customers via the graphical user interface 740. The graphical user interface 740 may be in communication with the historian 720 and the processor 730. All available data such as measurements, processed data, and the like thus will be easily accessible. The data acquisition system 710 may be in communication with the valves 260 and the sensors 380 and the other components herein via one or more data busses 760. VAMS 700 may operate unattended, without user interaction. Other components and other configurations may be used herein.

The data acquisition system 710 may be positioned locally at the steam turbine system 100 and/or remotely at a customer's location. A number of data acquisition systems 710 may be in communication with a client acquisition system 745. The client acquisition system 745 may have a similar configuration and components. Moreover, the historian 720 at the client acquisition system 745 at the customer site may collect data across multiple steam valves 260. The data acquisition systems 710 and/or the client acquisition systems 745 also may be in communication with a central data center 770. The central data center 770 may be in communication with the data acquisition systems 710 and or the client acquisition systems 745 via a virtual private network or the Internet 780 via a data collection in transmission tool 765, a secure file transfer, and the like. Further processing may be performed at the central data center 770. Other components and other configurations may be used herein.

References are made to block diagrams of systems, methods, apparatuses, and computer program products according to example embodiments. It will be understood that at least some of the blocks of the block diagrams, and combinations of blocks in the block diagrams, may be implemented at least partially by computer program instructions. As described above, these computer program instructions may be loaded onto a general purpose computer, a special purpose computer, a special purpose hardware-based computer, or other type of programmable data processing apparatus to produce a machine, such that the instructions that execute on the computer or other programmable data processing apparatus create means for implementing the functionality of at least some of the blocks of the block diagrams, or combinations of blocks in the block diagrams discussed below.

These computer program instructions also may be stored in a non-transitory, computer-readable memory that can direct the computer or other programmable data processing apparatus to function in a particular manner, such that the instructions stored in the computer-readable memory produce an article of manufacture including instruction means that implement the functions specified in the block or blocks. The computer program instructions also may be loaded onto a computer or other programmable data processing apparatus to create a series of operational steps to be performed on the computer or other programmable apparatus to produce a computer implemented process such that the instructions that are executed on the computer or other programmable apparatus provide steps for implementing the functions specified in the block or blocks.

One or more components of the systems and one or more elements of the methods described herein may be implemented through an application program running on an operating system of a computer. They also may be practiced with other computer system configurations, including hand held devices, multiprocessor systems, microprocessor-based or programmable consumer electronics, mini-computers, mainframe computers, and the like. Application programs that are components of the systems and methods described herein may include routines, programs, components, data structures, and so forth that implement certain abstract data types and perform certain tasks or actions. In a distributed computing environment, the application program (in whole or in part) may be located in local memory or in other storage. In addition, or alternatively, the application program (in whole or in part) may be located in remote memory or in storage to allow for circumstances where tasks are performed by remote processing devices linked through a communications network.

VAMS 700 thus may provide real time monitoring of the various valves and actuators. Specifically, VAMS 700 thus may provide real time status information, messages, warnings, and lifetime consumption information so as to provide determinations and predictions by comparing the actual data to design data. The following modules describe different types of inspection and monitoring techniques and methods that may be used herein. Many other and different modules and methods may be used herein, separately or together.

Figure 6:
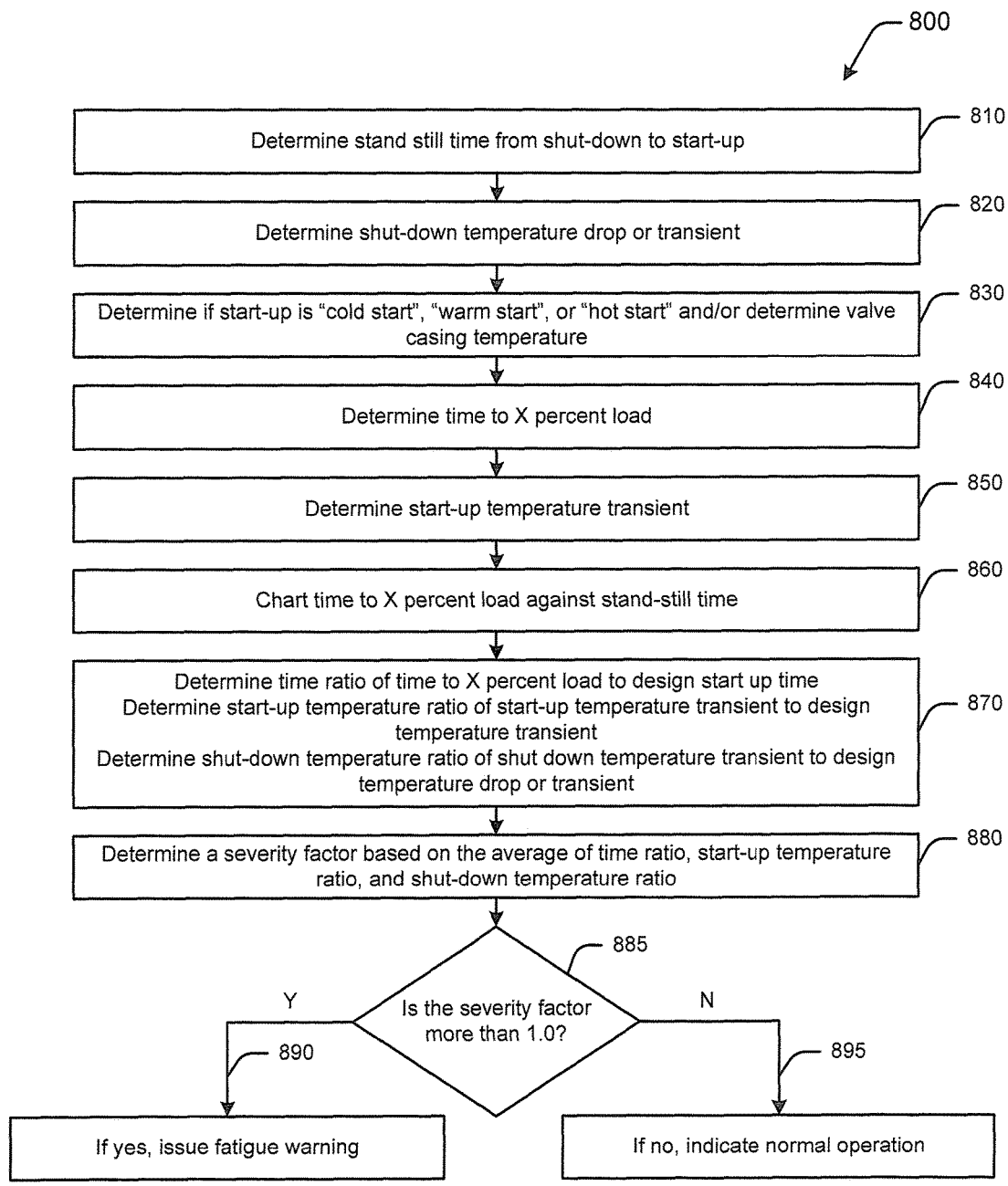
FIG. 6 is a flow chart of exemplary method steps in an Advanced Start-up Counter Module for use with VAMS of FIG. 5.

FIG. 6 shows a flow chart of example method steps for use in an Advanced Start-up Counter Module 800 as may be described herein. A conventional steam turbine generally counts the number of cold starts, warm starts, and hot starts. The Advanced Start-up Counter module 800 gathers further and more powerful information so as to provide estimations on low cycle fatigue damage. Specifically, the Advanced Start-up Counter Module 800 counts the number of starts and allocates to each start-up information concerning the shut-off period, the shut-down temperature drop, the start-up time, and the like. The Advanced Start-up Counter Module 800 creates a list of the start-ups and further information and then determines a severity indicator of the extent of possible fatigue damage.

By way of example, VAMS 700 gathers operating turbine and valve parameters from a number of sensors 380 and determines a number of operating conditions. Specifically at step 810, VAMS 700 determines a stand-still time from the last shut-down to the current start-up. Shut-down and start-up status may be determined by the position of the stop valves 270 via the position sensor 590 or from a signal of the turbine controller or from any other source. The valves and the actuators may be permanently monitored herein. At step 820, VAMS 700 may determine the shut-down temperature drop, i.e., the temperature decrease during the shut-down period. Alternatively or additionally, a temperature transient during the shut-down period may be determined. At step 830, VAMS 700 may determine if the start-up is a "cold start", a "warm start", or a "hot start" and/or VAMS 700 may determine the valve casing temperature via one of the metal temperature sensors 400, 410. The number and nature of the starts may be displayed and provided to the operator. The type of start-up (cold start, warm start, or hot start, for example) also may be read from signals from the turbine controller.

At step 840, VAMS 700 may determine the times to X % load of the steam turbine. The X % load may be set at 10% of load, 20% of load, . . . , 100% of load, or any percentage in between. At step 860, VAMS 700 may chart and display the time to X % load against the stand-still time. The chart may show all starts in the life of a particular valve or the turbine in general. Design data also may be used so as to compare design times to actual times.

At step 870, VAMS 700 may determine a number of ratios of actual data compared to design data. This may include a time ratio of a design start-up time to a time to X % load, a start-up temperature ratio of a start-up temperature transient to a design temperature transient, and a shut-down temperature ratio of the shut-down temperature drop or transient to a design temperature drop or transient. At step 880, VAMS 700 may determine a severity factor based on the average of the time ratio, the start-up temperature ratio, and/or the shut-down temperature ratio and/or a severity factor based on the maximum of these ratios. Alternatively, a severity factor based on the average of all the time ratios of all starts since the beginning of turbine operation or since the last valve inspection or since any other time point may be determined by the VAMS 700. In the same way, a severity factor based on the average of all of the start-up temperature ratios of all starts and a severity factor based on the average of all of the shut-down temperature ratios of all shut-downs may be determined.

The severity factors also may be used to determine a factorized sum of starts. Instead of counting x cold starts, y warm starts, and z hot starts, the factorized sum of starts may be a sum of the characteristic severity factors of all starts. A characteristic severity factor may be a value, characterizing the severity of one specific start. This may be determined by building the product of the time ratio, the start-up temperature ratio, and the shut-down temperature ratio or by building the product of these ratios, whereby each of the ratios is weighted with a weighting factor. Instead of the three values x, y, z for the number of starts, the factorized sum of the starts may be one value, which is a better indicator of the fatigue damage, caused by all the start-ups and shut-downs in the time period of interest.

At step 885, VAMS 700 may determine if any one of these severity factors is more than 1.0. If so, VAMS 700 may issue a fatigue warning at step 890. Such a fatigue warning may include not only displaying the information to the operator but also changing one or more of the operating parameter or operating conditions and/or initiating repair procedures and/or initiating exchange of valve parts. These operating parameters may include times, temperatures, and the like. If all of the severity factors are less than 1.0, VAMS 700 may indicate normal operation at step 895. In any event, current fatigue status will be displayed and available to the operator.

Shorter actual start-up times may mean higher severity. Likewise, higher actual temperature transients may mean higher severity. The Advanced Start-up Counter Module 800 thus provides the operator with a detailed overview of the start-up history and indicates in a simple way the possible low cycle fatigue damage. This information may be updated for each start. The Advanced Start-up Counter Module 800 thus may provide a more accurate description of possible fatigue damage as compared to known counters without the need for visual inspection and downtime. The Advanced Start-up Counter Module 800 thus can support the decision, when a valve inspection shall be performed, e.g., by defining an upper limit for the factorized sum of starts in between two inspections.

Figure 7:
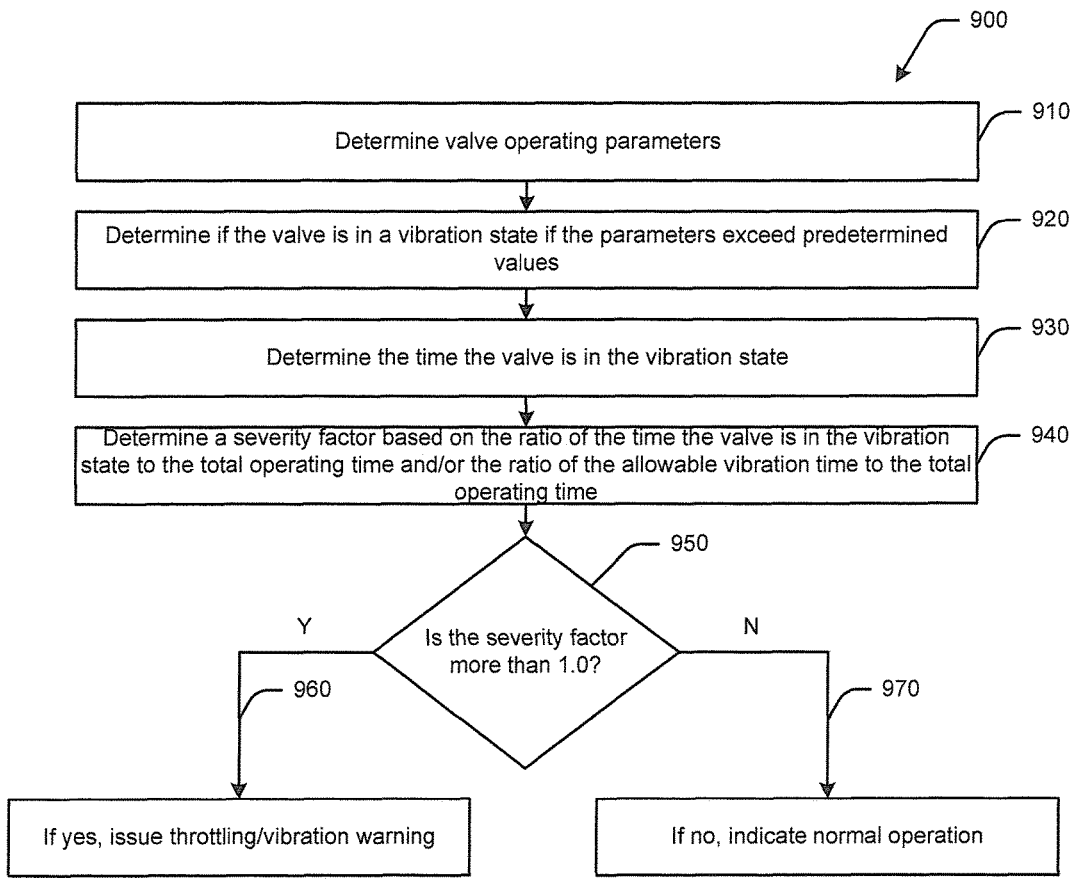
FIG. 7 is a flow chart of exemplary method steps in an Advanced Throttling Time Counter Module for use with VAMS of FIG. 5.

FIG. 7 shows example method steps in an Advanced Throttling Time Counter Module 900 as may be described herein. The Advanced Throttling Time Counter Module 900 indicates whether a given valve is operating in heavy throttling conditions. Specifically, when the valve bell and the like is in a certain position range and when the pressure ratio over the valve is in a certain range, then the valve may be vibrating strongly due to excitation under unstable steam flow. Such vibration may lead to increased wear and/or damage of the valve if this vibration occurs over a longer period of time.

By way of example, at step 910 VAMS 700 may determine different types of turbine and valve operating parameters. These operating parameter may include the pressure from the valve inlet pressure sensor 560 and the pressure drop over the valve from the valve inlet pressure sensor 560 and the high pressure valve pressure sensor 480 at the high pressure section 110, the intermediate pressure valve pressure sensor 490 at the intermediate pressure section 120, the position of the spindle via the spindle position sensor 590, the mass flow rate via the flow rate sensors 500, 510, and the like. The valves and the actuators may be permanently monitored. At step 920, VAMS 700 may determine if a valve is in a vibration state, i.e., if certain parameters exceed predetermined values. For example, whether the valve bell is in a certain position range and if the pressure ratio (i.e., pressure after the control valve seat divided by the pressure before the control valve seat) is in a certain range. The position and the pressure ratio ranges with high vibrations are determined experimentally or theoretical analysis, e.g., 3D flow analysis. At step 930, VAMS 700 may determine the time that the valve has been operated in the vibration state. At step 940, VAMS 700 may determine a severity factor based on the ratio of the time in the vibration state to the total operating time and on the ratio of the allowable vibration time to the total operating time. The allowable vibration time may be received by experience. At step 950, VAMS 700 may determine if the severity factor is more than 1.0. A ratio greater than 1.0 may indicate unfavorable throttling operation. At step 960, VAMS 700 may issue a throttling warning if the ratio is greater than 1.0. Such a throttling warning may include not only displaying the information to the operator but also changing one or more of the operating parameter or operating conditions and/or initiating repair procedures and/ or initiating an exchange of valve parts. The operating parameters may include changing pressure, temperature, spindle position, mass flow rate, and the like. If ratio is less than 1.0, VAMS 700 may indicate normal operation at step 970. In any event, current vibration status will be displayed to the operator. VAMS 700 also may provide statistics on how long the valve was operated at each stroke, accumulated vibration time. Excessive or unusual vibration also may be determined and reported.

The Advanced Throttling Time Counter 900 thus provides information on the likely wear and erosion condition of a given valve. The operator may better manage spare parts in that the operator only needs to order parts when needed or in advance of a planned inspection. Unnecessary spare parts do not need to be kept in stock. The Advanced Throttling Time Counter Module 900 thus gives the operator an overview of the accumulative vibration history of the valve. This history provides an indication for the wear of the guides and the erosion of the valve seats. The Advanced Throttling Time Counter Module 900 thus may provide a more accurate description of possible wear damage without the need for visual inspection and downtime.

Figure 8:
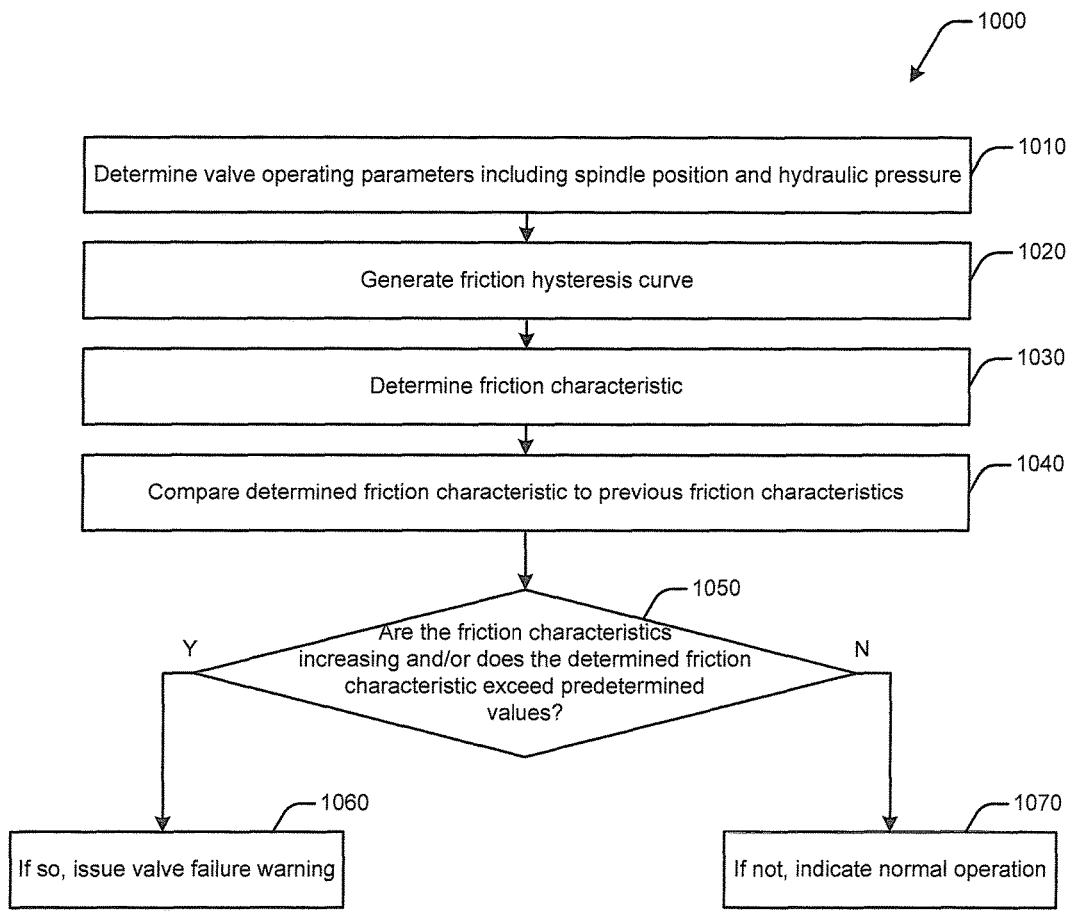
FIG. 8 is a flow chart of exemplary method steps in a Guiding Condition Assessment Module for use with VAMS of FIG. 5.

FIG. 8 is a flow chart showing exemplary method steps in a Guide Condition Assessment Module 1000 as may be described herein. The Guide Condition Assessment Module 1000 may measure and evaluate the friction behavior of the spindles in the steam valves 260. The resulting friction characteristics may be compared with previous measurements and a trend of the friction characteristics may be assessed. Such an assessment is in contrast to current inspection methods requiring the disassembly of the valves. These current methods may result in a leaking valve in between inspection intervals that may present an operational risk as well as health and safety issues.

Generally described, the spindle within each steam valve 260 may be guided within guide bushes or other guiding elements (such as bores in valves) and may be tightened to the outside, e.g., with graphite packings. Due to valve vibrations, ageing, corrosion, oxidation, wear, changing of roughness, erosion, particles in the steam and following deposits on the sliding faces, as well as changes to clearance due to deformation, the sliding behavior of the spindle at the guide elements and the spindle seals may change over time. Such changes may result in the spindle beginning to stick such that the valve may not be able to close properly or may result in loosening the pre-tension in the graphite seals. In order to assess the condition of the steam valves 230 at step 1010, VAMS 700 may obtain operational parameters such as the position of the spindle via the position sensor 590, steam pressure from the pressure sensors 480, 490, 560, as well as the hydraulic pressure of the high pressure oil in the actuators 340, 370 via the hydraulic pressure sensor 595. Other types of parameters also may be considered herein. The valves and the actuators may be permanently monitored. At step 1020, VAMS 700 may generate a friction hysteresis curve, i.e., the hydraulic pressure dependence of the spindle position during movement of the spindle first in closing and then in the opening position. The difference in the hydraulic pressure in the opening and the closing directions shows the static and sliding friction (static friction, when the spindle is stopping before the movement starts, e.g., at the turning point of the spindle movements; sliding friction, at those spindle positions, where the spindle is not stopping.) At step 1030, VAMS 700 may determine a friction characteristic. The friction characteristic may include the calculated static friction at the top and bottom turning point and the sliding friction with maximum, average, and minimum values and curves of static and sliding friction over the spindle way in both directions. Other types of friction characteristics may be evaluated herein. At step 1040, VAMS 700 may compare the determined friction characteristics, i.e., the friction values as described above, to friction characteristics from previous stroke tests. At step 1050, VAMS 700 may determine whether the friction characteristics are increasing and/or whether the determined friction characteristic exceeds a predetermined value. If so, a valve failure warning may be issued at step 1060. Such a valve failure warning may include not only displaying the information to the operator but also taking the valve off line, changing one or more of the operating parameters or operating conditions, and/or initiating repair procedures. The operating parameters may include hydraulic and steam pressure, spindle position, steam and metal temperatures, and the like. If not, normal operation may be indicated at step 1070.

The Guide Condition Assessment module 1000 thus may provide an operator with an early warning that a valve may be sticking. Such an early warning may allow the operator to re-tighten the spindle seals of the valve and/or order spare parts and/or plan for remachining of the guides to ensure correct clearances. Previously, an improperly working seal could only be detected during inspection or via the leakage during operation. The Guiding Condition Assessment Module 1000 thus insures that the valves provide sufficient steam tightness toward the environment and gives a pre-warning, when the valve guides are getting worse, before the event of a sticking valve occurs. The Guide Condition Assessment Module 1000 thus may provide a more accurate description of possible guide and seal damage without the need for visual inspection and downtime.

Figure 9:
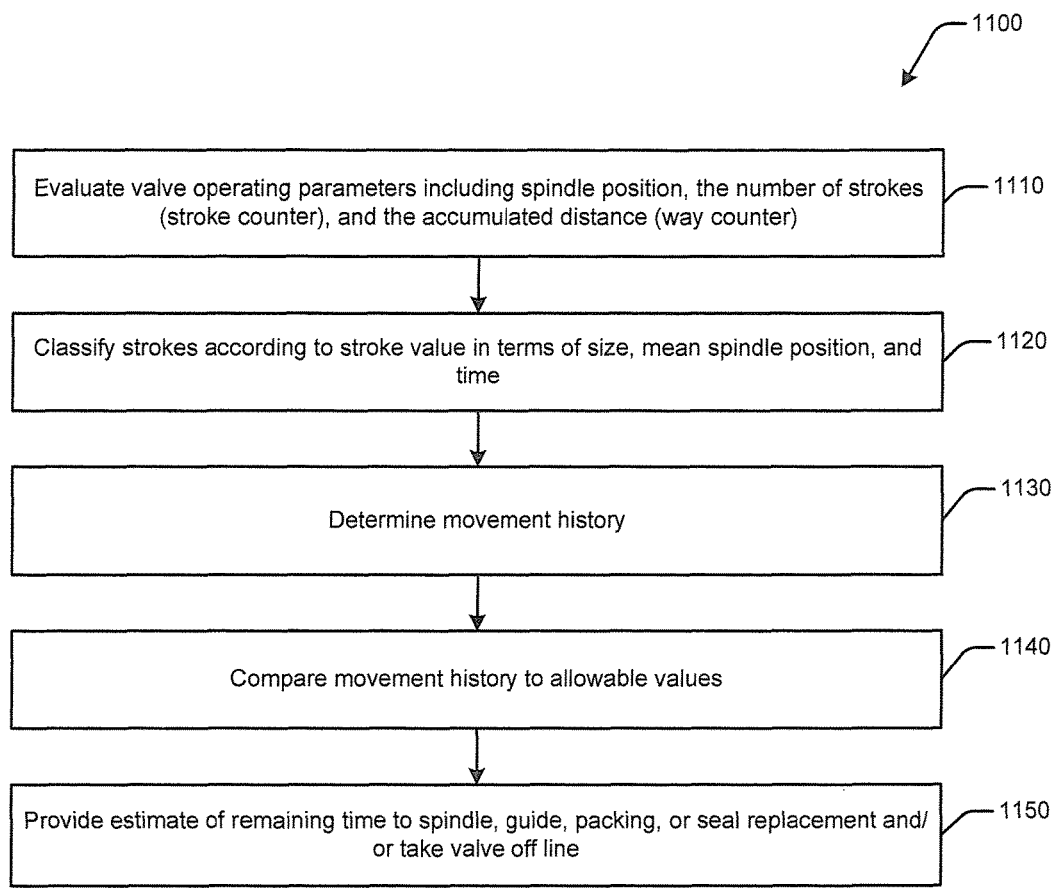
FIG. 9 is a flow chart of exemplary method steps in a Valve Stroke and Spindle Way Counter Module for use with VAMS of FIG. 5.

FIG. 9 is a flow chart showing exemplary method steps in a Valve Stroke and Spindle Way Counter Module 1100 as may be described herein. The wear of the internal spindle guide is influenced by the number of valve strokes and the covered distance of the valve head. The more strokes and the longer the covered distance, the more wear may be expected. Previously, the condition of the guides and the seals of the valve spindle could only be discovered by disassembling the valve.

The Valve Stroke and Spindle Way Counter Module 1100 thus counts the number of strokes (stroke counter) and counts the covered distance (way counter). Specifically, VAMS 700 at step 1110 obtains the time dependent spindle position from the position sensor 590 and counts the strokes and the covered distance. The valves and the actuators may be permanently monitored. At step 1120, VAMS 700 may classify the strokes according to stroke value, i.e., VAMS 700 may sort the strokes according to size (linear distributed ranges or sorted in geometrical series) and the mean spindle position. Further, the time that the spindle stays in a certain position also may be counted. The strokes may be considered small, medium, large or otherwise. When the valve is controlling, the spindle usually performs permanent small strokes. Such small strokes may be filtered out or removed from the overall statistics. The stroke values may be determined via a rainflow method, a range mean method, and the like. The rainflow method may be used in an analysis of spindle movement data in order to reduce a spectrum of varying spindle movement into a set of simple strokes. Specifically, the rainflow method is a method for counting cycles from a time history. Other types of cycle counting methods and spindle movement analysis may be used herein.

At step 1130, VAMS 700 may evaluate the overall spindle movement history. The movement history may be shown as scalar values, matrices, or diagrams. At step 1140, VAMS 700 may compare the movement history with known allowable values. Based upon this comparison, VAMS 700 may provide an estimate of the remaining time to guide replacement at step 1150. Depending upon the comparison, VAMS 700 also may take the valve off line, change one or more of the operating parameter or operating conditions, and/or initiate repair procedures, e.g., for repairing the spindle guides and/or the spindle seals. The estimates may be shown to the plant operator on a monitor or otherwise reported.

The Valve Stroke and Spindle Way Counter Module 1100 thus gives the plant operator permanently an overview of the current status of the movement history. Such movement history provides an indication of the wear of the guides and the spindle seals and whether the guides and the seals should be replaced now, at the next inspection, or otherwise. The plant operator may consider this information for inspection planning and for ordering spare parts. The valve parts may include worn guides, worn spindle, worn graphite packaging, and the like. Overall information concerning lifetime consumption and residual life also may be provided. The Valve Stroke and Spindle Way Counter Module 1100 thus may provide a more accurate description of possible guide wear without the need for visual inspection and downtime.

Figure 10:
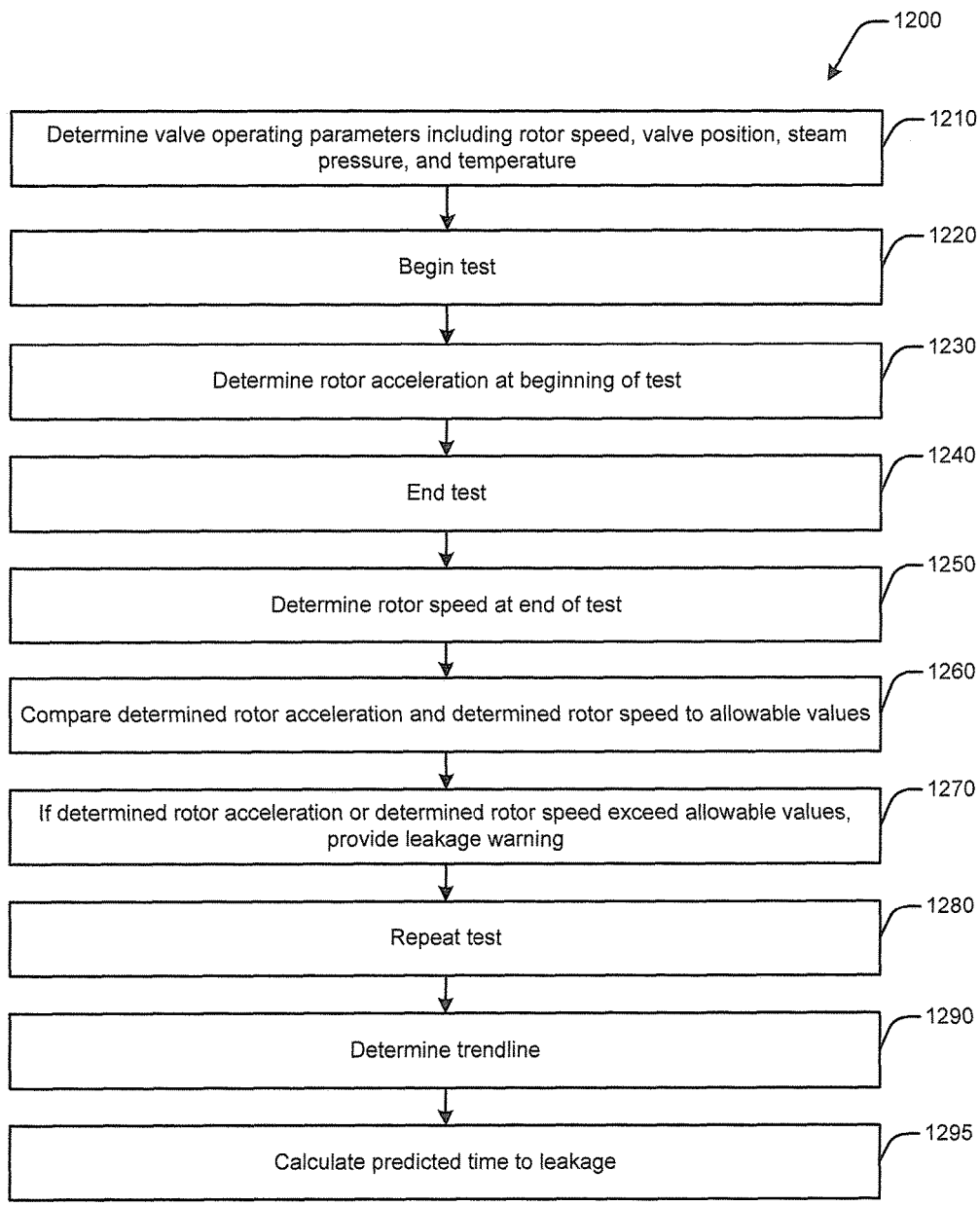
FIG. 10 is a flow chart of exemplary method steps in a Tightness Test Evaluation Module for use with VAMS of FIG. 5.

FIG. 10 is a flow chart of exemplary steps in a Tightness Test Evaluation Module 1200 as may be described herein. The Tightness Test Evaluation Module 1200 may give the plant operator an overview of the current status of the tightness of the valves in comparison to the past measurements. Specifically, the Tightness Test Evaluation Module 1200 may provide an indication of the status of the piston rings and any erosion at the valve seat to determine whether the piston rings, the bell, the diffuser, and the like should be replaced now, at the next inspection, or otherwise. Further, the Tightness Test Evaluation Module 1200 compares the tightness tests of the turbine throughout the overall operation history and determines whether there is a trend of increasing valve leakage and hence valve damage.

By way of example, VAMS 700 may obtain turbine and valve operating parameters such as rotor speed from the rotor speed sensor 390, valve position from the position sensor 590, steam pressure from the pressure sensors 470, 480, 490, and temperature from the temperature sensors 420, 430, 440, 450, 460. The valves and the actuators may be permanently monitored. At step 1210, VAMS 700 may begin the tightness test. The beginning of the test may coincide with the opening of the stop valve 270. At step 1230, the rotor acceleration directly after opening the stop valve 270 may be measured. At step 1240, the test may be ended and the rotor speed may be determined at the end of the test at step 1250. At step 1260, VAMS 700 may compare the determined rotor acceleration and the determined rotor speed to allowable values. At step 1270, VAMS 700 may provide the operator with a leakage warning if the determined rotor acceleration and/or the determined rotor speed exceed allowable values. Specifically, the Tightness Test Evaluation Module 1200 determines whether the steam flow through the valve at a closed position is below the allowable limit. The allowable limit may be defined by the increase in the rotor speed and/or by the increase of the rotor acceleration. Such a valve failure warning may include not only displaying the information to the operator but also taking the valve off line, changing one or more of the operating parameter or operating conditions, and/or initiating repair procedures. The operating parameters may include speed, pressure, temperature, spindle position, and the like.

After a predetermined interval, the tightness test may be repeated at step 1280. At step 1290, VAMS 700 may compare the results of repeated tightness tests (rotor speed at the end of the test, acceleration at the beginning of the test) and different kinds of trend lines may be calculated, i.e., straight and exponential. At step 1295, VAMS 700 may calculate a predicted time to an unacceptable leakage based on the trendlines. The plant operator may consider this prediction for inspection planning and in ordering spare parts. The Tightness Test Evaluation Module 1200 thus gives the plant operator an overview of the current status of the tightness of the valves in comparison to the past. The plant operator thus may have warning about insufficient tightness before reaching critical values. The Tightness Test Evaluation Module 1200 thus may provide a more accurate description of valve tightness without the need for visual inspection and downtime.

Figure 11:
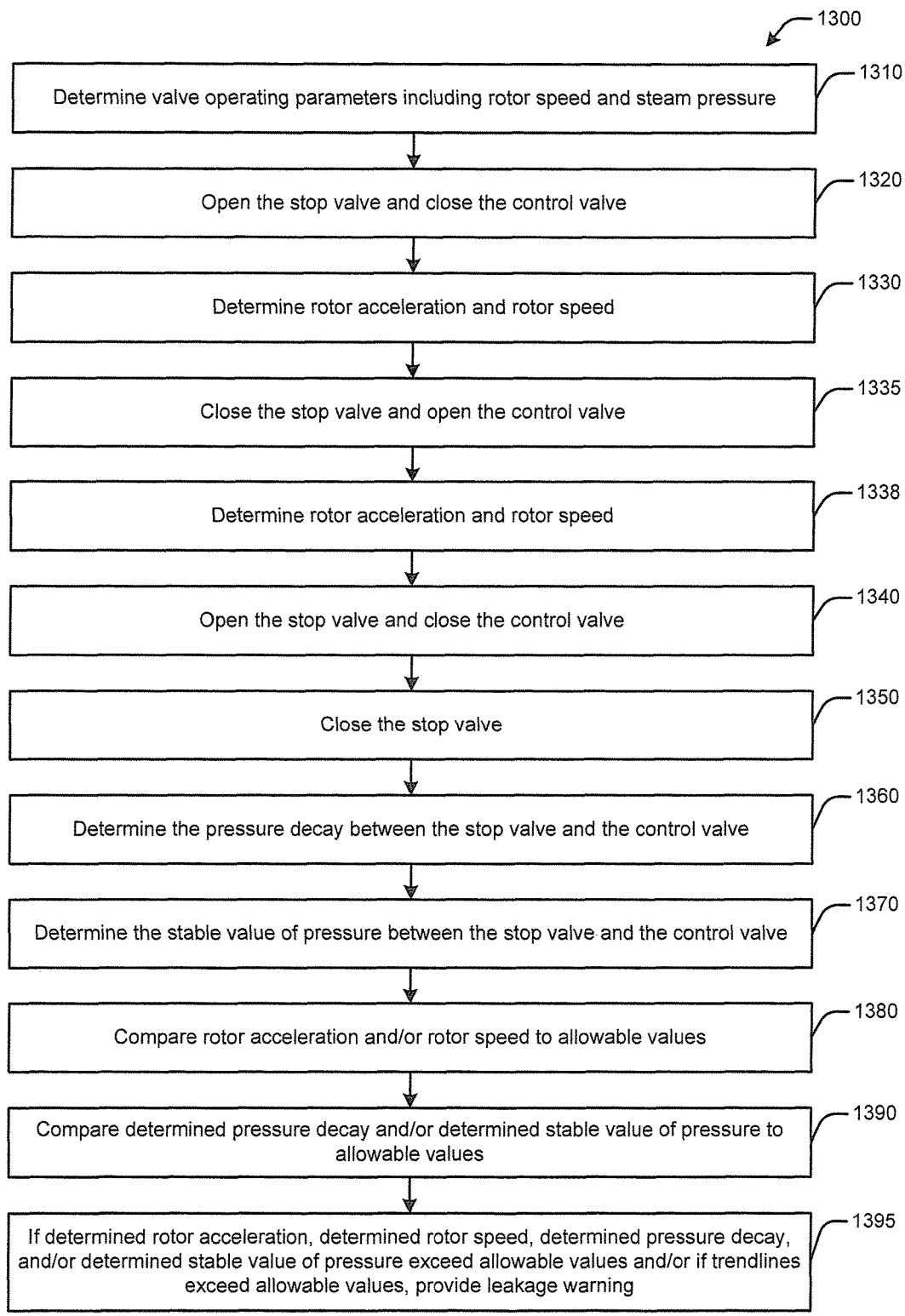
FIG. 11 is a flow chart of exemplary method steps in an Advanced Tightness Test Evaluation Module for use with VAMS of FIG. 5.

FIG. 11 is a flow chart showing example method steps in an Advanced Tightness Test Evaluation Module 1300 as may be described herein. Similar to the Tightness Test Evaluation Module 1200 described above, the Advanced Tightness Test Evaluation Module 1300 is a further enhancement using pressure decay and stable pressure values as an alternative and/or as an additional indicator for valve tightness and health. Insufficient tightness may point to erosion damage or other damage or misalignment at the valve seat or in other valve components.

By way of example, at step 1310 VAMS 700 may determine turbine and valve operating parameters including rotor speed from the rotor speed sensor 390 and steam pressures at various positions such as upstream of the stop valve 270, downstream of the control valve 280, and therebetween from the pressure sensors 480, 490, 560. At step 1320, the stop valve 270 may be open and the control valve 280 may be closed. At step 1330, rotor acceleration and rotor speed may be determined so as to provide an indication for the condition of the control valve seat. In a second mode of operating at step 1335, the stop valve 270 may close and the control valve 280 may open. At step 1338, rotor acceleration and rotor speed may be determined, giving an indication for the condition of the stop valve seat. In a third mode of operation at step 1340, the stop valve 270 may be opened and the control valve 280 may be closed. The stop valve 270 then may be closed at step 1350. At step 1360, the pressure decay between the stop valve 270 and the control valve 280 may be determined, e.g., measured with the middle pressure sensor 575. At step 1370, a stable pressure value may be determined once the pressure between the stop valve 270 and the control valve 280 has reached a stable value. At step 1380, VAMS 700 compares the rotor acceleration and/or the rotor speed measured above to allowable values. Likewise, or in the alternative at step 1390, VAMS 700 may compare the determined pressure decay (e.g., via the time constant or the difference of pressure in the beginning and after some time) and/or the determined stable value of pressure to allowable values. At step 1395, the determined rotor acceleration, the determined rotor speed, the determined pressure decay, and/or the determined stable value of pressure may be compared with measurements from previous tests and the trendline for each type of measurement may be analyzed. If the trendlines show an increase larger than an allowable increase or if the trendlines show that the measurements come close to the allowable limits, then VAMS 700 may provide a leakage warning. Such a leakage warning may include not only displaying the information to the operator but also taking the valve off line, changing one or more of the operating parameter or operating conditions, and/or initiating repair procedures. The operating parameters may include speed, pressure, temperature, spindle position, and the like. Specifically, if the allowed values are exceeded, valve erosion may have occurred and the valve components may need to be replaced now, at the next inspection, or otherwise.

The Advanced Tightness Test Module 1300 may be done automatically at each turbine start or on demand. The plant operator may consider this information for inspection planning and to prepare spare parts in advance. The Advanced Tightness Test Module 1300 thus gives the plant operator a more accurate description of valve tightness without the need for visual inspection and downtime.

Figure 12:
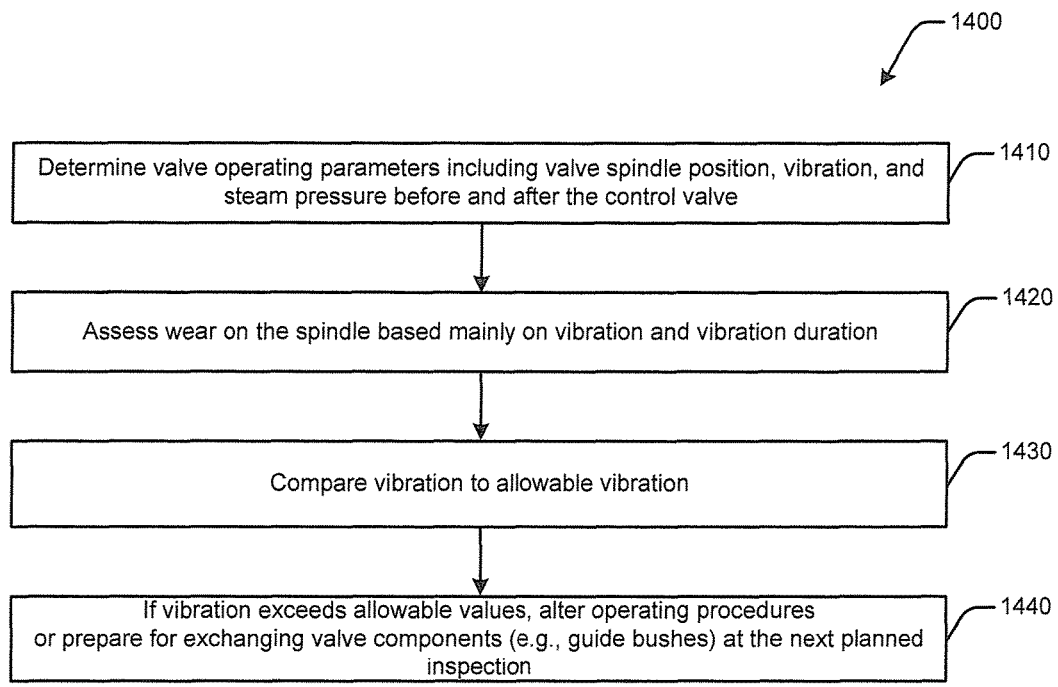
FIG. 12 is a flow chart of exemplary method steps in a Spindle Vibration Evaluation Module for use with VAMS of FIG. 5.

FIG. 12 is a flow chart of exemplary method steps in a Spindle Vibration Evaluation Module 1400 as may be described herein. The Spindle Vibration Evaluation Module 1400 may observe and evaluate the nature of the vibrations of the valve spindles. Such vibration may cause wear of the spindles and the related guide bushes and damage therein.

By way of example at step 1410, VAMS 700 may determine turbine and valve operating parameters including valve spindle position from the position sensor 590, spindle vibration levels from the vibration sensor 580, and steam pressure upstream and downstream of the valve from the pressure sensors 480, 490, 560, 575. At step 1420, the wear on the spindle and the guide bushes may be assessed mainly from the vibration sensor 580, i.e., evaluating the vibration characteristics (e.g., frequency and amplitude or frequency and vibration velocity) and the duration of the vibrations. At step, 1430, the vibration and the duration may be compared to predetermined values. Based upon this assessment, the plant operator may determine if replacement of the spindle or the guide bushes may be required, for example, at the next planned outage. In addition and/or alternatively, the plant operator may change the overall steam turbine mode of operation so as to reduce the level of vibration at step 1440. For example, one valve may be open slightly more and one valve may be open slightly less. VAMS 700 also may take the valve out of service and/or initiate repair procedures.

The Spindle Vibration Evaluation Module 1400 thus gives the plant operator an overview on the vibration behavior of the valve and the ability to change the operating parameters back into a safe zone. The operator thus can prepare for planned inspections and order spare parts in advance. Moreover, the relationship between steam pressure, spindle position, and vibration level may be recorded and provided to the plant operator and/or valve designer. The Spindle Vibration Evaluation Module 1400 thus may provide a more accurate description of vibration behavior without the need for visual inspection and downtime.

Figure 13:
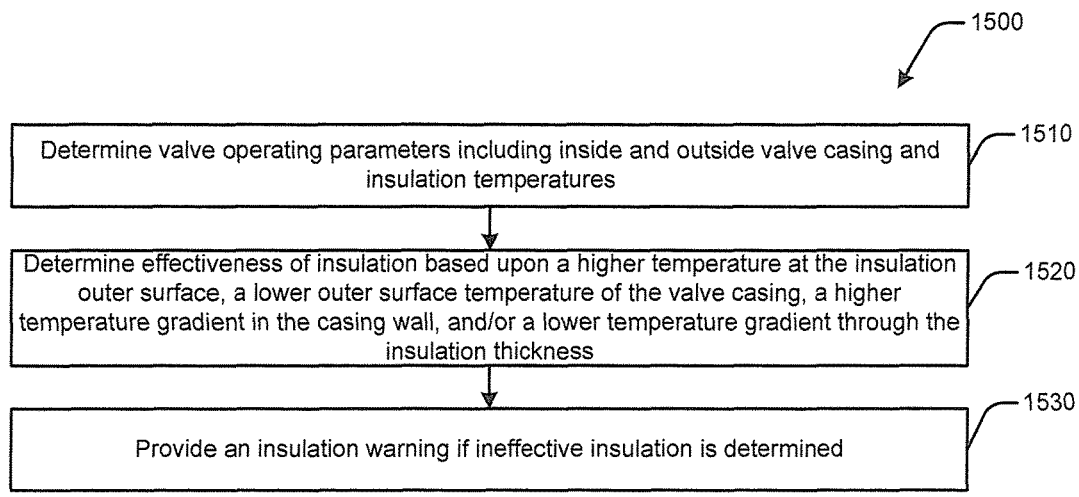
FIG. 13 is a flow chart of exemplary method steps in an Insulation Quality Indicator Module for use with VAMS of FIG. 5.

FIG. 13 is a flow chart showing example method steps in an Insulation Quality Indicator Module 1500 as may be described herein. The Insulation Quality Indicator Module 1500 performs, preferably automatically and permanently or on request, temperature measurements and evaluates, preferably automatically and permanently or on request, the effectiveness of the valve insulation 315. For example, whether the insulation 315 is ineffective due to aging or improper reassembly after an inspection of the valve casing.

By way of example at step 1510, VAMS 700 may determine turbine and valve operating parameters including inside and outside casing and insulation temperatures from the inner and outer casing temperature sensors 520, 530, 540, 550, and/or from dedicated insulation sensors. Specifically, temperatures may be determined at the metal surface of the casing, inside the insulation, at the surface of the insulation, and/or at the surface of metal sheets outside the insulation. A double measurement within the casing wall thickness also may determine a temperature gradient through the casing wall. Similar temperature gradients through the insulation also may be determined. Thermographic sensors and the like also may be used to produce a thermographic picture of the whole insulated valve or of parts of the insulation surface. At step 1520, VAMS 700 may determine the effectiveness of the insulation. A less effective insulation may be shown by a higher temperature at the insulation outer surface, a lower temperature at the outer surface of the casing wall, a higher temperature gradient through the casing wall, and/or a lower temperature gradient through the insulation thickness. At step 1530, VAMS 700 may provide an insulation warning if it is determined that the insulation is ineffective. Such an insulation warning may include not only displaying the information to the operator but also taking the valve off line or changing one or more of the operating parameter or operating conditions. The plant operator then may correct the insulation, order spare parts, and/or plan inspections.

The Insulation Quality Indicator Module 1500 thus gives the plant operator a more accurate overview of the condition of the valves and turbine. The Insulation Quality Indicator Module 1500 provides an indication of whether the insulation is effective as intended. If not, a warning may be provided that the insulation is no longer effective due to wrong assembly, aging, and the like. The Insulation Quality Indicator Module 1500 thus may provide a more accurate description of valve insulation without the need for visual inspection and downtime.

Figure 14:
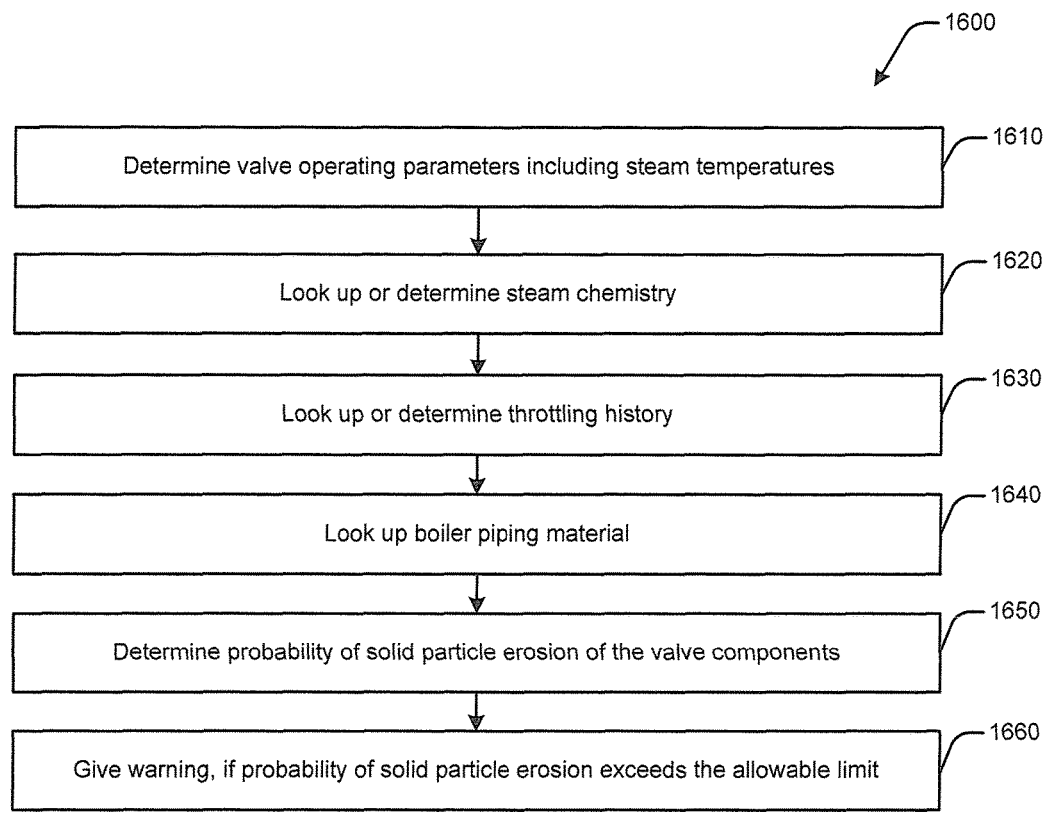
FIG. 14 is a flow chart of exemplary method steps in a Solid Particle Erosion Indicator Module for use with VAMS of FIG. 5.

FIG. 14 is a flow chart showing exemplary method steps in a Solid Particle Erosion Indicator Module 1600 as may be described herein. The Solid Particular Erosion Indicator Module 1600 evaluates the temperature of the boiler pipeline and nature of the pipeline material so as to assess the risk of scaling therein. Temperature transients and steam velocities in the boiler pipeline may influence when the scaling is detaching from the boiler pipes and flowing with the steam into the valve. The steam chemistry also may influence how fast scaling is build up in the pipe lines. Scaling may lead to erosion of the valve and other types of turbine components, especially when the valve is throttling and high local steam velocities may occur, e.g., at the diffuser seat and the valve bell or valve head.

By way of example in step 1610, VAMS 700 may determine turbine and valve operating parameters including incoming steam temperatures from the boiler 160 in the high pressure line 180 via the high pressure inlet temperature sensor 420, 450 and including steam temperatures from the reheater 200 in the intermediate pressure line 210 via the intermediate pressure inlet temperature sensors 410, 460. Metal temperature sensors at the pipe wall also may be used. At step 1620, VAMS 700 may look up or determine the nature of the steam chemistry of the incoming steam flow or of the condensing water in the steam/water cycle of the power plant. At step 430, VAMS 700 may look up or determine the throttling history of the valve in question. By way of example, the throttling history may be determined by the Advanced Throttling Time Counter Module 900 described above. Other types of counters and the like also may be used herein. At step 1640, VAMS 700 may look up the type of boiler piping material used on the high pressure line 180 or elsewhere. At step 1650, VAMS 700 may determine the probability of solid particle erosion of the valve components based upon the steam temperature and its transient, the steam chemistry, the throttling history, the boiler piping material, and the like. The probability also may be evaluated on the timely coincidence of measurements, e.g., when throttling occurs and at the same time a strong temperature gradient is present, leading to a high flow of solid particles from the boiler pipe and at the same time to high local speeds in the valve internals and therefore a high damaging effect. The probability of erosion damage may be accumulated over the time. At step 1660, VAMS 700 may compare the current probability and/or accumulated probability with allowable values. Depending upon the nature of the probability, VAMS 700 may take the valve off line or changing one or more of the operating parameter or operating conditions. The plant operator then may order spare parts and/or plan inspections. The solid particle erosion indicator module 1600 is also useful as one of several modules of an inspection interval counter.

The Solid Particle Erosion Indicator Module 1600 thus gives the plant operator a more accurate overview of the condition of the valve parts with respect to erosion. The VAMS 700 may perform this evaluation automatically. The Solid Particle Erosion Indicator Module 1600 thus may provide a more accurate description of possible erosion damage without the need for visual inspection and downtime.

Figure 15:
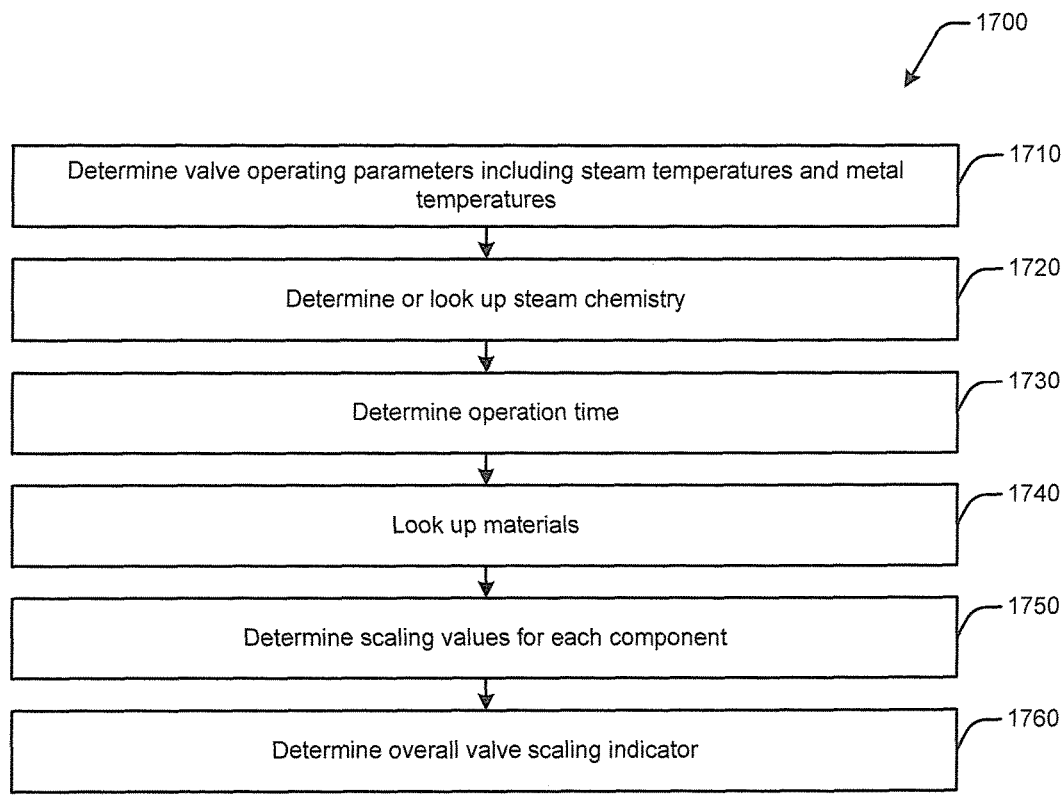
FIG. 15 is a flow chart of exemplary method steps in a Scaling Indicator Module for use with VAMS of FIG. 5.

FIG. 15 is a flow chart showing exemplary method steps in a Scaling Indicator Module 1700 as may be described herein. The Scaling Indicator Module 1700 may assess the scaling of the valve and other turbine components based on temperature measurements, steam chemistry, and material type. The Scaling Indicator Module 1700 may provide a predicted scaling status.

By way of example at step 1710, VAMS 700 may determine turbine and valve operating parameters including steam temperatures from the various steam temperature sensors 420, 430, 440, 450, 460 and metal temperatures from the metal temperature sensors 400, 410 preferably over the whole valve operation time. At step 1720, VAMS 700 may determine or look up the steam chemistry of the flow of steam preferably over the whole valve operation time. At step 1730, VAMS 700 may determine the overall turbine operation time. At step 1740, VAMS 700 may look up the nature of the materials involved in the various valve components. At step 1750, VAMS 700 may determine a scaling value for each valve component based on the temperature history, steam chemistry history, and the nature of the material of each valve component. At step 1760, VAMS 700 may provide an overall valve scaling indicator based on the nature of the main materials in the valve. Specifically, VAMS 700 may provide a prediction of the condition of the various valve components based upon actual operation time with respect to scaling. Depending upon the nature of the risk, VAMS 700 may take the valve off line or changing one or more of the operating parameter or operating conditions. The plant operator then may order spare parts and/or plan inspections.

The Scaling Indicator Module 1600 thus gives the plant operator a more accurate overview of the condition of the valve parts with respect to scaling of the valve components. The Scaling Indicator Module 1600 provides a prediction as to when parts should be replaced. Based upon these results, the plant operator may better prepare for plant inspections and or spare parts. The Scaling Indicator Module 1600 thus may provide a more accurate description of possible valve scaling damage without the need for visual inspection and downtime.

Figure 16:
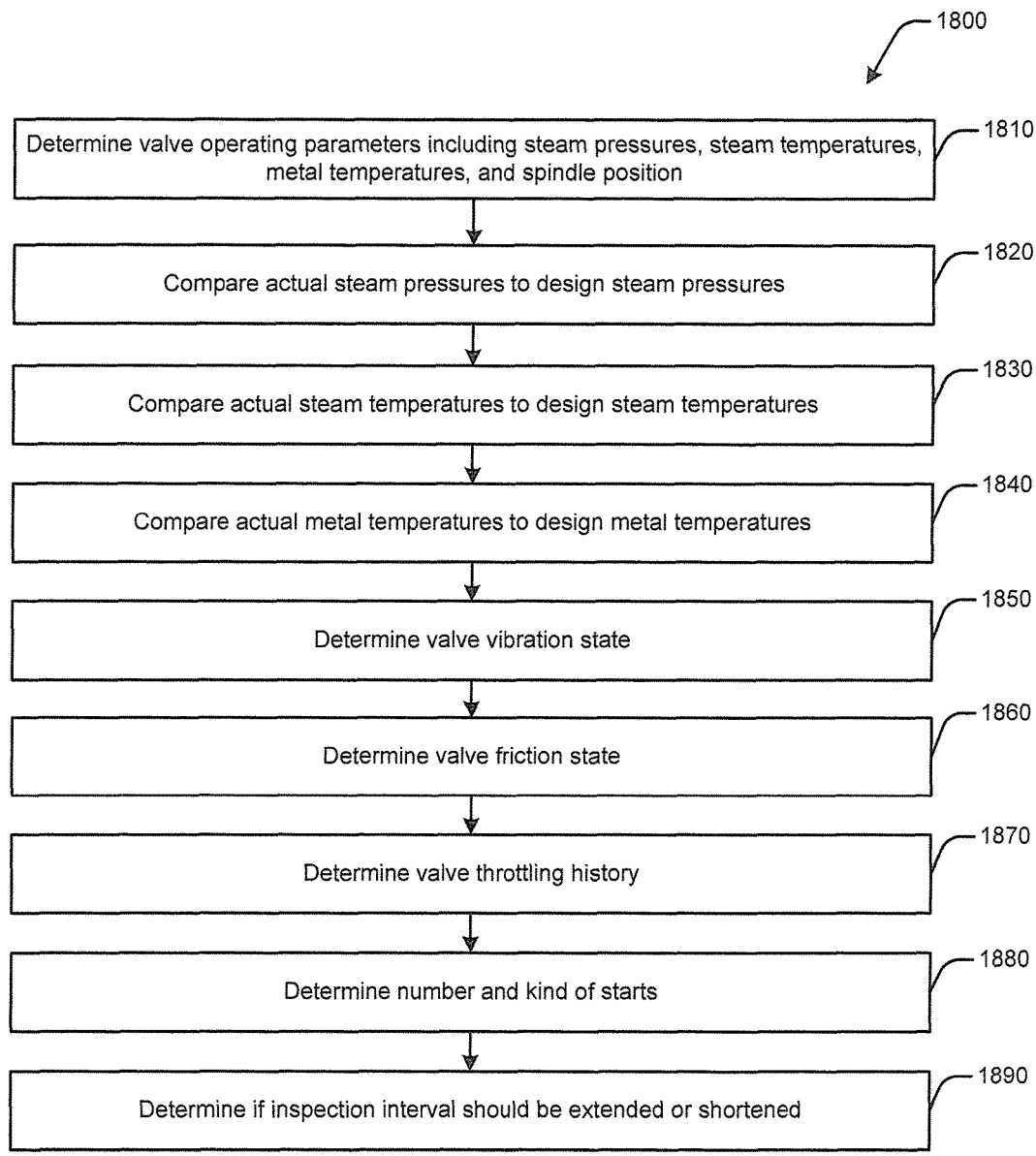
FIG. 16 is a flow chart of exemplary method steps in a Flexible Service Counter Module for use with VAMS of FIG. 5.

FIG. 16 shows a flow chart of exemplary method steps in a Flexible Service Interval Counter Module 1800 as may be described herein. The Flexible Service Interval Counter Module 1800 may determine if the inspection intervals should be expanded or shortened based on the overall operation of the valve.

By way of example at step 1810, VAMS 700 may determine turbine and valve operating parameters including steam pressure from the pressure sensors 470, 480, 490, 560, 575, steam temperatures from the temperature sensors 420, 430, 440, 450, 460, metal temperatures from the metal temperature sensors 400, 410, 520, 530, 540, 550, the position of the spindle as determined by the position sensor 590, the hydraulic pressure in the actuator as determined by the hydraulic pressure sensor 595, the turbine speed determined by the speed sensor 390, and the steam chemistry. At step 1820, VAMS 700 may compare the actual steam pressures to design steam pressures. At step 1830, VAMS 700 may compare the actual steam temperatures to design steam temperatures. At step 1840, VAMS 700 may compare the actual metal temperatures to design metal temperatures. At step 1850, VAMS 700 may determine the valve vibration state. By way of example, the Advanced Throttling Time Counter Module 900 may be used to determine the vibration state. Other types of analysis may be used. At step 1860, the valve friction state may be determined. By way of example, the Guide Condition Assessment Module 1000 may be used to herein. Other types of analysis may be used. At step 1870, the valve throttling history may be determined. At step 1880, the number and kind of starts may be determined. By way of example, the advanced Start Counter Module 800 may be used herein. Other types of analysis may be used. At step 1890, VAMS 700 may consider each of these valve operational parameters and the evaluated, damage indicators to recommend that the inspection interval be extended or shortened and/or if the valve should be taken off line.

Specifically, the Advanced Throttling Time Counter Module 900 gives to the plant operator the residual operation time until an inspection is recommended. For example, when the valve is operated all the time at relatively low temperature and pressure, then the recommended inspection interval, i.e., the operation time in between two inspections, may be extended as compared to the standard interval, whereas when the valve is operated all the time at relatively high temperature and pressure, then the recommended inspection interval may be reduced as compared to the standard value. High erosion probability, as detected by the erosion indicator, may reduce the recommended inspection interval. High detected leakage through the valve seat, as measured and evaluated with the Tightness Test Indicator or the Advanced Tightness Test Indicator, may reduce the recommended inspection interval. High creep damage as detected by a creep damage indicator may reduce the recommended inspection interval. Relatively long throttling times, especially when the stroke position is in a critical area concerning vibrations, as e.g., detected by the Advanced Throttling Time Counter, may reduce the recommended inspection interval. High vibrations over longer time as evaluated with the Spindle Vibration Evaluation module may reduce the recommended inspection interval. Unfavorable steam chemistry, measured over a longer time, may reduce the recommended inspection interval. High scaling as detected by the Scaling Indicator Module may reduce the recommended inspection interval.

The Flexible Service Interval Counter Module 1800 thus provides the plant operator a recommendation on the time point of the next inspection. This recommendation is based on the nature of the operation of the turbine and other influences. This inspection may be performed automatically. Specifically, the inspection interval may be extended when the valve is operating smoothly at low engine conditions. Inspection intervals may be shortened if any of the operational parameters exceed allowed values. The Flexible Service Interval Counter Module 1800 thus may provide a more accurate description of valve conditions without the need for visual inspection and downtime.

VAMS 700 thus provides a permanent on-line valve and actuator monitoring product for steam turbines. Condition monitoring of the steam valves 260 provides vital information on the health of the valves and the steam turbine system 100 as a whole. The monitored information may allow the operator to make decisions to ensure optimal machine performance as well as provide early warning of possible failures by detecting different valve failure symptoms at an early stage. VAMS 700 provides the operator with assessment reports suggesting measures to reduce outage costs and time, modify operating conditions to reduce lifetime consumption, and transitions from time based maintenance to condition based maintenance to extend overall maintenance intervals.

It should be apparent that the foregoing relates only to certain embodiments of the present application and the resultant patent. Numerous changes and modifications may be made herein by one of ordinary skill in the art without departing from the general spirit and scope of the invention as defined by the following claims and the equivalents thereof.

I claim:

1. A method of evaluating insulation quality in a turbine by a data acquisition system, comprising:
   receiving a plurality of operating parameters from a plurality of sensors;
   wherein the plurality of operating parameters comprises casing temperatures and insulation temperatures;
   comparing the casing temperatures and the insulation temperatures to predetermined casing and insulation values; and
   altering one or more of the plurality of operating parameters and/or initiating repair procedures if the casing temperatures fall below the casing predetermined values and/or the insulation temperatures exceed the insulation predetermined values.

2. The method of claim 1, wherein the step of altering one or more of the plurality of operating parameters and/or initiating repair procedures comprises taking a valve out of service.

3. The method of claim 1, wherein the step of altering one or more of the plurality of operating parameters and/or initiating repair procedures comprises repairing or replacing an insulation layer.

4. The method of claim 1, wherein the casing temperatures are determined by an inner wall casing temperature sensor and an outer wall casing temperature sensor.

5. The method of claim 1, wherein the plurality of operating parameters comprises a thermal gradient through the casing wall.

6. The method of claim 5, wherein the temperature gradient is determined by a thermographic sensor.

7. The method of claim 5, wherein a temperature field on the insulation is compared to the insulation predetermined values or to previous temperature fields to locate an insulation hot spot.

8. The method of claim 5, further comprising the steps of comparing the temperature gradient to a predetermined gradient value and altering one or more of the plurality of operating parameters and/or initiating repair procedures if the temperature gradient exceeds the predetermined gradient value.

9. The method of claim 1, wherein the plurality of operating parameters comprises a thermal gradient through the insulation.

10. A turbine system, comprising:
    a plurality of valves;
    a plurality of sensors capable of receiving turbine and valve operating parameters; and
    a data acquisition system, including a processor in communication with the plurality of sensors and wherein the data acquisition system is operable to perform the following operations:
    receiving the plurality of turbine and valve operating parameters from the plurality of sensors;
    wherein the plurality of turbine and valve operating parameters comprises casing temperatures and insulation temperatures;
    comparing the casing temperatures and the insulation temperatures to predetermined values; and
    providing a warning if the casing temperatures and/or the insulation temperatures exceed or fall below the predetermined values.

11. The turbine system of claim 10, wherein the data acquisition system is further operable to take a valve out of service if the casing temperatures and/or the insulation temperatures exceed or fall below the predetermined values.

12. The turbine system of claim 10, wherein the data acquisition system is further operable to alter one or more of the plurality of turbine and valve operating parameters if the casing temperatures and/or the insulation temperatures exceed or fall below the predetermined values.

13. The turbine system of claim 10, wherein the data acquisition system is further operable to initiate repair procedures if the casing temperatures and/or the insulation temperatures exceed or fall below the predetermined values.

14. The turbine system of claim 10, wherein the data acquisition system is further operable to order parts if the casing temperatures and/or the insulation temperatures exceed or fall below the predetermined values.

15. The turbine system of claim 10, wherein the plurality of valves comprises one or more steam stop valves and one or more stream control valves.

* * * * *